United States Patent
Staubli et al.

(10) Patent No.: US 9,492,543 B2
(45) Date of Patent: Nov. 15, 2016

(54) COMPOSITIONS FOR TREATING COGNITIVE DISORDERS

(71) Applicant: Allergan, Inc., Irvine, CA (US)

(72) Inventors: Ursula V. Staubli, Laguna Beach, CA (US); John E. Donello, Dana Point, CA (US)

(73) Assignee: Allergan, Inc., Irvine, CA (US)

( * ) Notice: Subject to any disclaimer, the term of this patent is extended or adjusted under 35 U.S.C. 154(b) by 0 days.

(21) Appl. No.: 13/649,404

(22) Filed: Oct. 11, 2012

(65) Prior Publication Data

US 2013/0040938 A1  Feb. 14, 2013

Related U.S. Application Data

(62) Division of application No. 12/838,019, filed on Jul. 16, 2010, now abandoned.

(60) Provisional application No. 61/226,425, filed on Jul. 17, 2009.

(51) Int. Cl.
| | |
|---|---|
| *A61K 31/4427* | (2006.01) |
| *A61K 31/4523* | (2006.01) |
| *A61K 31/439* | (2006.01) |
| *A61K 45/06* | (2006.01) |
| *A61K 31/40* | (2006.01) |
| *A61K 31/4025* | (2006.01) |
| *A61K 31/4409* | (2006.01) |
| *A61K 31/4709* | (2006.01) |

(52) U.S. Cl.
CPC .............. *A61K 45/06* (2013.01); *A61K 31/40* (2013.01); *A61K 31/4025* (2013.01); *A61K 31/4409* (2013.01); *A61K 31/4427* (2013.01); *A61K 31/4523* (2013.01); *A61K 31/4709* (2013.01)

(58) Field of Classification Search
None
See application file for complete search history.

(56) References Cited

U.S. PATENT DOCUMENTS

| | | | |
|---|---|---|---|
| 4,166,452 A | 9/1979 | Generales | |
| 4,256,108 A | 3/1981 | Theeuwes | |
| 4,265,874 A | 5/1981 | Bonsen | |
| 2007/0049576 A1* | 3/2007 | Barlow et al. | 514/214.03 |
| 2008/0070901 A1 | 3/2008 | Tracey | |
| 2009/0036436 A1 | 2/2009 | Leblond | |
| 2010/0048642 A1* | 2/2010 | Donello et al. | 514/343 |
| 2010/0093793 A1* | 4/2010 | Donello et al. | 514/314 |
| 2010/0190792 A1* | 7/2010 | Donello et al. | 514/237.8 |

FOREIGN PATENT DOCUMENTS

| | | |
|---|---|---|
| WO | 2008-109285 A1 | 9/2008 |
| WO | 2008-109287 A1 | 9/2008 |
| WO | 2008-109610 A1 | 9/2008 |
| WO | WO 2008109286 A1 * | 9/2008 |
| WO | 2009-012082 A1 | 1/2009 |

OTHER PUBLICATIONS

Psychiatric Mental Health Nurse Practitioner Review & Resource Manual—2nd Edition, May 2008, p. 211-226, Ed. Karen Guess, MSN, PMHNP, ANP-BC, Chapter 10—Cognitive Disorders.*
Lanctot et al., Efficacy and safety of cholinesterase inhibitors in Alzheimer's disease: A meta-analysis, CMAJ, Sep. 16, 2003; 169(6): 557-564.*
Cristina Lanni, et al., Cognition Enhancers Between Treating and Doping the Mind, Pharmacological Research, 2008, 196-213, 57, Elsevier, US.
David B. Hogan, et al., Management of Mild to Moderate Alzheimer's Disease and Dementia, Alzheimer's & Dementia, 2007, 355-384, 3, Elsevier, US.
Francesca Mangialasche, et al., Alzheimer's Disease: Clinical Trials and Drug Development, The Lancet Neurology, Jul. 2010, 16 Pages, 9, US.
Nathan Herrman, et al., Clinical Practice Guidelines for Severe Alzheimer's Disease, Alzheimer's & Dementia, 2007, 385-397, 3, Elsevier, US.
Remingtons, Remingtons_16th, Pharmaceutical Sciences, 1980, 1-10, 16, Remingtons_16th.
Stephen Salloway, et al., Disease Modifying Therapies in Alzheimer's Disease, Alzheimer's & Dementia, 2008, 65-79, 4 (2), Elsevier, US.
Ursula Staubli, et al., Studies on Long-Term Depression in Area CA1 of the Anesthitized and Freely Moving Rat, The Journal of Neuroscience, Jun. 15, 1997, 4820-4829, 17 (12), US.

* cited by examiner

*Primary Examiner* — Svetlana M Ivanova
(74) *Attorney, Agent, or Firm* — Jonathan Bass (57) ABSTRACT

Disclosed herein is a pharmaceutical composition comprising a cholinesterase inhibitor and compound of the following formula:

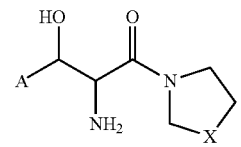

The composition is effective for treating cognitive disorders, and methods of treating such disorders using the composition are also disclosed.

6 Claims, 3 Drawing Sheets

COMPOSITIONS FOR TREATING COGNITIVE DISORDERS

CROSS REFERENCE TO RELATED APPLICATIONS

This application is a divisional of U.S. Ser. No. 12/838,019, filed Jul. 16, 2010 which claims the benefit of U.S. Provisional Patent Application Ser. No. 61/226,425, filed on Jul. 17, 2009, the entire disclosure of which is incorporated herein by this specific reference.

Disclosed herein is a pharmaceutical composition comprising a cholinesterase inhibitor and a compound represented by Formula I:

wherein X is $CH_2$ or $CH_2$—$CH_2$,
A is aryl or heteroaryl having 0, 1, 2, or 3 heteroatoms selected from the group consisting of N, S, and O,
wherein A has 0, 1, 2, or 3 substituents independently selected from the group consisting of 0 to 8 carbon atoms, from 0 to 3 oxygen atoms, from 0 to 3 halogen atoms, from 0 to 2 nitrogen atoms, from 0 to 2 sulfur atoms, and from 0 to 24 hydrogen atoms.

The composition is effective for treating cognitive disorders, and methods of treating such disorders using the composition are also disclosed. Cholinesterase inhibitors have many undesirable side effects, such as nausea, diarrhea, insomnia, muscle cramps, sweating, and trembling.

The inventors have discovered that administering the compounds of Formula I with a cholinesterase inhibitor allows one to treat cognitive disorders using significantly lower doses of cholinesterase inhibitors—in some embodiments, as low as one-tenth the usual dose or even lower—thereby providing an effective treatment with fewer side effects.

DETAILED DESCRIPTION OF THE INVENTION

Cholinesterase Inhibitors

The term "cholinesterase inhibitor," as used here, means a compound that inhibits the enzymatic degradation of the neurotransmitter acetylcholine, thereby increasing the duration of action of acetylcholine and its levels in the synaptic cleft. Two enzymes are principally responsible for the degredation of acetylcholine, acetylcholinesterase and butyrylcholinesterase. "Cholinesterase inhibitor" includes compounds that inhibit or otherwise reduce the action of one or both of those enzymes.

The compositions and methods of the invention contemplate that the cholinesterase inhibitors be pharmaceutically effective. "Pharmaceutically effective," as used here, means that the cholinesterase inhibitor is therapeutically useful in humans. The term therefore excludes those cholinesterase inhibitors used as pesticides, such as aldicarb(2-methyl-2-(methylthio)propionaldehyde O-methylcarbamoyloxime), carbofuran(2,3-dihydro-2,2-dimethyl-7-benzofuranyl methylcarbamate), and carbaryl(1-naphthyl methylcarbamate), and those cholinesterase inhibitors that are so toxic to humans that they are used as chemical weapons, such as sarin(2-(fluoro-methylphosphoryl)oxypropane), VX (S-[2-(diisopropylamino)ethyl]-O-ethyl methylphosphonothioate), and soman(3-(fluoro-methyl-phosphoryl)oxy-2,2-dimethyl-butane). Most cholinesterase inhibitors that are pesticides and chemical weapons are quasi-reversible or irreversible; most cholinesterase inhibitors that are pharmaceutically effective are reversible.

Pharmaceutically effective cholinesterase inhibitors are well known in the art. U.S. Patent Application Publication No. 2008/0070901, for example, the contents of which are incorporated herein by reference, discloses that cholinesterase inhibitors include 7-methoxytacrine, alvameline, ambenonium, anseculin, arecoline, cevimeline, citicoline, demacarium, donepizil, edrophonium, eptastigmine, fasciculin, heptyl-physostigmine, huperzine A and its analogs, icopezil, ipidacrine, linopiridine, metrifonate, milameline, neostigmine, nomeostigmine, norpyridostigmine, tacrine, physostigmine, rivastigmine, subcomeline, suronacrine, tacrine analogs, tacrine, talsaclidine, velnacrine, xanomeline, zifrosilone, and various others. One can use in the compositions and methods of the invention any of these compounds.

At least three pharmaceutically effective cholinesterase inhibitors have been used in humans to treat dementia. These include donepezil, galantamine, and rivastigmine.

Donepezil is a reversible inhibitor of acetylcholinesterase. It has the following structure

The hydrochloride salt of donepezil is sold in the United States under the brand name Aricept®. Donepezil is indicated for the treatment of dementia of the Alzheimer's type. It is administered at an adult dose of 5 mg or 10 mg once per day. Because of the possibility of adverse events, the 10 mg dose is not administered until patients have been on a dose of 5 mg/day for 4 to 6 weeks. The most common adverse events, defined as those occurring in at least 5% in patients receiving 10 mg/day and twice the placebo rate, include nausea, diarrhea, insomnia, vomiting, muscle cramp, fatigue and anorexia.

Galantamine is a reversible inhibitor of acetylcholinesterase. It has the following structure:

The hydrobromide salt of galantamine is sold in the United States under the brand name Razadyne®. Galantamine is indicated for the treatment of mild to moderate dementia of the Alzheimer's type. It is administered at an adult dose of between 16-24 mg/day given as twice-daily dosing. The starting dose is 4 mg twice a day (8 mg/day), increased after 4 weeks to 8 mg twice a day (16 mg/day), and then increased after another 4 weeks to 12 mg twice a day (24 mg/day). The most frequent adverse events, defined as those occurring at a frequency of at least 5% and at least twice the placebo rate, include nausea, vomiting, diarrhea, anorexia, and weight decrease.

Rivastigmine is a reversible cholinesterase inhibitor having the following structure:

Rivastigmine tartrate is sold in the United States under the brand name Exelon®. Rivastigmine is indicated for the treatment of mild to moderate dementia of the Alzheimer's type, and for the treatment of mild to moderate dementia associated with Parkinson's disease. Rivastigmine is administered at an adult dose of 6-12 mg/day, given as twice-a-day dosing (daily doses of 3 to 6 mg BID). The starting dose is 1.5 mg twice a day, and, if well tolerated, is increased after a minimum of 2 weeks of treatment to 3 mg twice a day. After an additional 2 weeks of treatment the dose is further increased to 4.5 mg twice a day, and, 2 weeks later, to 6 mg twice a day, unless adverse events occur requiring lower doses. The most frequent adverse events, defined as those occurring at a frequency of at least 5% and at least twice the placebo rate, include nausea, vomiting, anorexia, dyspepsia, and asthenia.

Other pharmaceutically effective cholinesterase inhibitors that have been widely used to treat conditions in humans include physostigmine, pyridostigmine, and neostigmine.

Compounds of Formula I

The compositions and methods of the invention include, in addition to a cholinesterase inhibit, the compounds of Formula I:

wherein X is $CH_2$ or $CH_2$—$CH_2$,

A is aryl, or is heteroaryl having 0, 1, 2, or 3 heteroatoms selected from the group consisting of N, S, and O, wherein A has 0, 1, 2, or 3 substituents each comprising 0 to 8 carbon atoms, from 0 to 3 oxygen atoms, from 0 to 3 halogen atoms, from 0 to 2 nitrogen atoms, from 0 to 2 sulfur atoms, and from 0 to 24 hydrogen atoms.

"Aryl," as used here, means any ring or ring system that contains at least one aromatic ring.

"Heteroaryl," as used here, means an aromatic ring in which 0, 1, 2, or 3 of the atoms in the ring are N, S, or O; this includes, for example, pyridinyl, thienyl, and furyl.

The substituents may be the same or different. Examples of substituents having the constraints defined here include, but are not limited to, the following:

hydrocarbyl, meaning a moiety consisting of carbon and hydrogen only, including, but not limited to,
  a. alkyl, meaning hydrocarbyl having no double or triple bonds, including, but not limited to,
    i) linear alkyl, e.g. methyl, ethyl, n-propyl, n-butyl, n-pentyl, n-hexyl, etc.,
    ii) branched alkyl, e.g. iso-propyl, t-butyl and other branched butyl isomers, branched pentyl isomers, etc.,
    iii) cycloalkyl, e.g. cyclopropyl, cyclobutyl, cyclopentyl, cyclohexyl, etc., which may optionally be fused to another cycloalkyl or phenyl substituent;
    iv) combinations of linear, branched, and/or cycloalkyl;
  b. alkenyl, e.g. hydrocarbyl having 1 or more double bonds, including linear, branched, or cycloalkenyl;
  c. alkynyl, e.g. hydrocarbyl having 1 or more triple bonds, including linear or branched (alkynyl);
  d. combinations of alkyl, alkenyl, and/or akynyl;

alkyl-CN, such as —$CH_2$—CN, —$(CH_2)_2$—CN; —$(CH_2)_3$—CN, and the like;

hydroxyalkyl, i.e., alkyl-OH, such as hydroxymethyl, hydroxyethyl, and the like;

ether substituents, including —O-alkyl, alkyl-O-alkyl, and the like;

hydroxy alkyl ether, such as —COOH, thioalkyl and thioether substituents, including —S-alkyl, alkyl-5-alkyl, and the like;

amine substituents, including —NH$_2$, —NH-alkyl, —N-alkyl$^1$alkyl$^2$ (i.e., alkyl$^1$ and alkyl$^2$ are the same or different, and both are attached to N), alkyl-NH$_2$, alkyl-NH-alkyl, alkyl-N-alkyl$^1$alkyl$^2$, and the like;

aminoalkyl, meaning alkyl-amine, such as aminomethyl (—CH$_2$-amine), aminoethyl, and the like;

ester substituents, including —CO$_2$-alkyl, —CO$_2$-phenyl, etc.;

other carbonyl substituents, including aldehydes; ketones, such as acyl (i.e.

and the like; in particular, acetyl, propionyl, and benzoyl substituents are contemplated;

phenyl and substituted phenyl; the phenyl and substituted phenyl may itself be optionally fused with another phenyl or cycloalkyl substituent;

fluorocarbons and hydrofluorocarbons such as —CF$_3$, —CH$_2$CF$_3$, etc.;

—CN; and

—F, —Cl, —Br, or —I.

Combinations of the foregoing substituents are also possible, subject to the constraints defined.

Substituents must be sufficiently stable to be useful for any purpose disclosed herein.

If a substituent is a salt, for example of a carboxylic acid or an amine, the counter-ion of said salt, i.e. the ion that is not covalently bonded to the remainder of the molecule is not counted for the purposes of the number of heavy atoms in a substituent. Thus, for example, the salt —CO$_2$$^-$Na$^+$ is a stable substituent consisting of 3 heavy atoms, i.e. sodium is not counted. In another example, the salt —NH(Me)$_2$$^+$Cl$^-$ is a stable substituent consisting of 3 heavy atoms, i.e. chlorine is not counted.

In one embodiment, A is pyridinyl, meaning that compounds of structures such as those shown below are contemplated. In these structures, R1, R2, and R3 are substituents as defined herein:

In another embodiment, A is thienyl, meaning that compounds of structures such as those shown below are contemplated. In these structures, R1 and R2 are substituents as defined herein:

In another embodiment, A is furyl, meaning that compounds of structures such as those shown below are contemplated. In these structures, R1, R2, and R3 are substituents as defined herein:

In one embodiment, each substituent is independently alkyl having from 1 to 8 carbon atoms.

In another embodiment, A is unsubstituted or has an isopropyl substituent.

In another embodiment, each substituent of B is —F, —Cl, —CH$_3$, or —CF$_3$.

In another embodiment, A is pyridyl, thienyl, furyl, pyrrolyl, pyrrolidinyl, imidazolyl, oxazolyl, thiazolyl, pyrazolyl, pyrimidinyl, quinolinyl, or pyrazinyl having 0, 1, 2, or 3 substituents.

Unless otherwise indicated, reference to a compound includes pharmaceutically acceptable salts, tautomers, alternate solid forms, and non-covalent complexes of a chemical entity of the depicted structure or chemical name.

A pharmaceutically acceptable salt is any salt of the parent compound that is suitable for administration to an animal or human. A salt comprises one or more ionic forms of the compound, such as a conjugate acid or base, associated with one or more corresponding counter-ions. Salts can form from or incorporate one or more deprotonated acidic groups (e.g. carboxylic acids), one or more protonated basic groups (e.g. amines), or both (e.g. zwitterions).

Pharmaceutically acceptable salts of acidic functional groups may be derived from organic or inorganic bases. The salt may comprise a mono or polyvalent ion. Of particular interest are the inorganic ions, lithium, sodium, potassium, calcium, and magnesium. Organic salts may be made with amines, particularly ammonium salts such as mono, di and trialkyl amines or ethanol amines. Salts may also be formed with caffeine, tromethamine and similar molecules. Hydrochloric acid or some other pharmaceutically acceptable acid may form a salt with a compound that includes a basic group, such as an amine or a pyridine ring.

Tautomers are isomers that are in rapid equilibrium with one another. They often, but do not necessarily, include a transfer of a proton, hydrogen atom, or hydride ion. For example, the structures herein are intended to include, but are not limited to, the tautomeric forms shown below:

Unless stereochemistry is explicitly depicted, a structure includes every possible stereoisomer, both pure or in any possible mixture.

Alternate solid forms are different solid forms than ones that may result from practicing the procedures described herein. For example, alternate solid forms may be polymorphs, different kinds of amorphous solid forms, glasses, and the like.

Non-covalent complexes are complexes that may form between the Compound and one or more additional chemical species that do not involve a covalent bonding interaction between the Compound and the additional chemical species. They may or may not have a specific ratio between the Compound and the additional chemical species. Examples might include solvates, hydrates, charge transfer complexes, and the like.

Methods for producing the compounds of Formula I are described in, for example, U.S. Patent Application Publication No. 2009/0036436, the disclosure of which is incorporated herein by reference.

Compositions useful in the method of the invention may further include an excipient. Such an excipient may be a carrier or a diluent; this is usually mixed with the active compound, or permitted to dilute or enclose the active compound. If a diluent, the carrier may be solid, semi-solid, or liquid material that acts as an excipient or vehicle for the active compound. The formulations may also include wetting agents, emulsifying agents, preserving agents, sweetening agents, and/or flavoring agents.

Cognitive Disorders

The term "cognitive disorder," as used here, means any condition characterized by a deficit in mental activities associated with thinking, learning, or memory. Examples of such disorders include agnosias, amnesias, aphasias, apraxias, deliriums, dementias, and learning disorders.

In some cases, the cause of a cognitive disorder may be unknown or uncertain. In other cases, the cognitive disorder may be associated with (that is, be caused by or occur in the presence of) other conditions characterized by damage to or loss of neurons or other structures involved in the transmission of signals between neurons. Hence, cognitive disorders may be associated with neurodegenerative diseases such as Alzheimer's disease, corticobasal degeneration, Creutzfeldt-Jacob disease, frontotemporal lobar degeneration, Huntington's disease, multiple sclerosis, normal pressure hydrocephalus, organic chronic brain syndrome, Parkinson's disease, Pick disease, progressive supranuclear palsy, or senile dementia (Alzheimer type); it may be associated with trauma to the brain, such as that caused by chronic subdural hematoma, concussion, intracerebral hemorrhage, or with other injury to the brain, such as that caused by infection (e.g., encephalitis, meningitis, septicemia) or drug intoxication or abuse; and may be associated with Down syndrome and Fragile X syndrome.

Cognitive disorders may also be associated with other conditions which impair normal functioning of the central nervous system, including psychiatric disorders such as anxiety disorders, dissociative disorders, mood disorders, schizophrenia, and somatoform and factitious disorders; it may also be associated with conditions of the peripheral nervous system, such as chronic pain.

The compounds described here may be used to treat agnosias, amnesias, aphasias, apraxias, deliriums, dementias, learning disorders and other cognitive disorders regardless of whether their cause is known or not.

Examples of dementias which may be treated with the methods of the invention include AIDS dementia complex, Binswanger's disease, dementia with Lewy Bodies, frontotemporal dementia, multi-infarct dementia, Pick's disease, semantic dementia, senile dementia, and vascular dementia.

Examples of learning disorders which may be treated with the methods of the invention include Asperger's syndrome, attention deficit disorder, attention deficit hyperactivity disorder, autism, childhood disintegrative disorder, and Rett syndrome.

Examples of aphasia which may be treated with the methods of the invention include progressive non-fluent aphasia.

The compounds described here may also be used to treat patient having deficits in mental activities that are mild or that otherwise do not significantly interfere with daily life. Mild cognitive impairment is an example of such a condition: a patient with mild cognitive impairment displays symptoms of dementia (e.g., difficulties with language or memory) but the severity of these symptoms is such that a diagnosis of dementia may not be appropriate. The compounds described here may be used to treat mild cognitive impairment and other, similarly less severe forms of cognitive disorders.

Pharmaceutical Compositions

Pharmaceutical compositions of the invention comprise one or more pharmaceutically effective cholinesterase inhibitors and one or more compounds of Formula I.

Dose

The pharmaceutical compositions of the invention may be formulated such that a patient receives a dose of a cholinesterase inhibitor that is usually effective, when administered separately, to treat the cognitive disorder for which the cholinesterase inhibitor is indicated, and a dose of a compound of Formula I that is usually effective, when administered separately, to treat the cognitive disorder. But the pharmaceutical compositions of the invention may also be formulated such that doses of each compound may be those that are ineffective or minimally effective when the compounds are administered alone. This allows one to administer to a patient a formulation of the invention that is as effective as larger doses of cholinesterase inhibitors and compounds of Formula I administered alone, but that is less likely to lead to side effects. This does not mean, however, that formulations of the invention comprise cholinesterase inhibitors and compounds of Formula I in only such doses which are, when administered alone, minimally effective: a patient administered a composition comprising the usual dose of such compounds is likely to experience an improvement that is greater than the improvement the patient would experience when administered the compounds alone.

The precise dose and frequency of administration depends on the severity and nature of the patient's condition, on the manner of administration, on the potency and pharmacodynamics of the particular compound employed, and on the judgment of the prescribing physician. Determining dose is a routine matter that is well within the capability of someone of ordinary skill in the art. Doses of pain-relieving anticonvulsants for treating convulsions, discussed in previous sections, may moreover be used as a guide.

It may be desirable to administer a dose of the cholinesterase inhibitor and the compound of Formula I that is ineffective or minimally effective when the compounds are administered alone. Determining such a dose is a routine matter. Typical such doses are set forth below:

TABLE 2

Doses of cholinesterase inhibitors that are generally ineffective or minimally effective, when administered alone, to treat dementia in adult patients

| COMPOSITION | INEFFECTIVE DOSES |
| --- | --- |
| Donepezil | <5 to 10 mg once per day |
| Galantamine | <8 to 12 mg twice per day |
| Rivastigmine | <3 to 6 mg twice per day |

Should one desire to administer a dose of the cholinesterase inhibitor that is effective when administered alone, one can generally use in excess of the doses stated above.

Excipients and Dosage Forms

Those skilled in the art will readily understand that for administering pharmaceutical compositions of the invention the cholinesterase inhibitors and compounds of Formula I can be admixed with pharmaceutically acceptable excipient which are well known in the art.

A pharmaceutical composition to be administered systemically may be confected as a powder, pill, tablet or the like, or as a solution, emulsion, suspension, aerosol, syrup or elixir suitable for oral or parenteral administration or inhalation.

For solid dosage forms or medicaments, non-toxic solid carriers include, but are not limited to, pharmaceutical grades of mannitol, lactose, starch, magnesium stearate, sodium saccharin, the polyalkylene glycols, talcum, cellulose, glucose, sucrose and magnesium carbonate. The solid dosage forms may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the technique described in U.S. Pat. No. 4,256,108, U.S. Pat. No. 4,166,452, and U.S. Pat. No. 4,265,874 to form osmotic therapeutic tablets for control release. Liquid pharmaceutically administrable dosage forms can, for example, comprise a solution or suspension of one or more of the presently useful compounds and optional pharmaceutical adjutants in a carrier, such as for example, water, saline, aqueous dextrose, glycerol, ethanol and the like, to thereby form a solution or suspension. If desired, the pharmaceutical composition to be administered may also contain minor amounts of nontoxic auxiliary substances such as wetting or emulsifying agents, pH buffering agents and the like. Typical examples of such auxiliary agents are sodium acetate, sorbitan monolaurate, triethanolamine, sodium acetate, triethanolamine oleate, etc. Actual methods of preparing such dosage forms are known, or will be apparent, to those skilled in this art; for example, see *Remington's Pharmaceutical Sciences*, Mack Publishing Company, Easton, Pa., 16th Edition, 1980. The composition of the formulation to be administered, in any event, contains a quantity of one or more of the presently useful compounds in an amount effective to provide the desired therapeutic effect.

Parenteral administration is generally characterized by injection, either subcutaneously, intramuscularly or intravenously. Injectables can be prepared in conventional forms, either as liquid solutions or suspensions, solid forms suitable for solution or suspension in liquid prior to injection, or as emulsions. Suitable excipients are, for example, water, saline, dextrose, glycerol, ethanol and the like. In addition, if desired, the injectable pharmaceutical compositions to be administered may also contain minor amounts of non-toxic auxiliary substances such as wetting or emulsifying agents, pH buffering agents and the like.

Methods of Treatment

The compositions and methods of the invention are useful for treating cognitive disorders. To "treat," as used here, means to deal with medically. It includes, for example, administering a compound of the invention to prevent the onset of a cognitive disorder as well as to alleviate its severity.

One can administer to a patient having a cognitive disorder a pharmaceutical composition comprising a cholinesterase inhibitor and a compound of Formula I. But one can also administer these compounds separately, administering one immediately after the other, or administering one within a short interval after the other (e.g., 5-15 minutes, or 15-30 minutes, or 30 minutes-1 hour), or administering one within a longer interval after the other (e.g., 1-2 hours, 2-4 hours, 4-6 hours, 6-12 hours, or 12-24 hours). One can also administer one compound more frequently than another, administering, for example, a cholinesterase inhibitor one or more times daily and a compound of Formula I two or more times daily (or vice versa).

EXAMPLES

The invention is illustrated further by the following examples.

Example 1

Basal Excitatory Synaptic Transmission in the Hippocampus and Cortex of the Freely Moving Rat Experiments were carried out in freely moving male Sprague-Dawley rats implanted with depth stimulating and recording electrodes in the hippocampus and olfactory cortex to (1) characterize the effect of a compound of Formula 1 ((2R,3S)-2-amino-3-hydroxy-3-(pyridin-4-yl)-1-(pyrrolidin-1-yl)propan-1-one) ("Compound X") on basal excitatory synaptic transmission, a measure positively associated with behavioral performance and encoding of information; and (2) determine a possible interaction on synaptic transmission when Compound X is coapplied with physostigmine and galantamine—both members of the cholinesterase inhibitor family which has pro-cognitive efficacy in Alzheimer's Disease patients.

Compound X by itself significantly enhanced hippocampal excitatory synaptic transmission, and was similarly effective at enhancing transmission in the olfactory cortex. Physostigmine and galantamine had marginal effects on synaptic transmission in hippocampus and cortex at the doses tested. Physostigmine and galantamine, when co-applied with Compound X, facilitated synaptic transmission to a degree that was significantly larger than the increase obtained with Compound X alone for both hippocampus and cortex. This synergism between two structurally and functionally very different classes of compounds suggests that the pro-cognitive effects of Compound X can be magnified with cholinergic compounds already approved for Alzheimer's disease.

Methods

Field excitatory post-synaptic responses (fEPSPs) evoked by electrical stimulation were recorded in freely moving animals with depth electrodes permanently implanted in the hippocampus and olfactory cortex. Experiment 1 compared the effect of one dose level (6 mg/kg ip) of Compound X on hippocampal and cortical fEPSPs with vehicle control data. Experiment 2 compared the effect of Compound X (6 mg/kg ip) combined with either physostigmine (0.1 mg/kg ip) or galantamine (1 mg/kg ip) on hippocampal and cortical fEPSPs with vehicle control data.

Subjects

Male Sprague Dawley rats, 3 months of age at the time of surgery, were used. The animals were housed individually and kept in a 12:12 light/dark cycle with food and water available ad libitum.

Preparation for Chronic Hippocampal and Cortical Electrophysiology

Preparation of animals with chronically implanted electrodes followed procedures essentially as described in earlier published work (U. Staubli and J. Scafidi, J. J. Neurosci. 17: 4820-4828 (1997)). For recordings from the hippocampus, the stimulating electrode was placed in the perforant path within the entorhinal cortex, and the recording electrode in the hilus of the hippocampal dentate gyrus. For recording from the olfactory cortex, the stimulating electrode was placed in the olfactory tract and the recording electrode in the layer I of the piriform cortex.

Recording From Freely Moving Rats

Ten days following recovery from surgery, the animals were acclimated to the recording cage as well as to the attachment of a recording lead to the head stage. Recording sessions began by adjusting current intensities (25-100 µA) and pulse width of the monophasic stimulation pulse (100-250 µsec) to produce a field excitatory postsynaptic potential (fEPSP) that was 50-60% of the maximum amplitude of the population-spike free response which typically ranged between 4 and 8 mV. Recording signals were amplified and filtered with a band pass of 1 Hz to 5 kHz and fed into a PC running specialized software (NacGather) that digitizes measures and stores the evoked responses. Baseline recording sessions where fEPSPs were evoked every 20 sec were conducted daily for 20-45 min for at least 3 days, and only animals exhibiting and maintaining adequate and stable evoked monosynaptic fEPSPs were selected for further study.

Drug Testing

Hippocampal animals (subjects with electrodes implanted into hippocampus) were randomly assigned to one of 3 groups, i.e., Compound X alone, Compound X plus physostigmine, physostigmine alone. Cortical animals (subjects with electrodes implanted into olfactory cortex) were randomly assigned to 5 groups, i.e., Compound X alone, Compound X plus physostigmine, physostigmine alone, Compound X plus galantamine, galantamine alone. For each test, baseline responses were recorded for at least 15 minutes to establish stability, followed by injection of vehicle solution (ddw) and recording for another 20 min to verify that the injection procedure or the vehicle did not affect baseline responses. If changes in baseline greater than +5% were observed, the experiment was terminated for that day. All other animals were injected with test compound 20 min after vehicle, and fEPSP recording was continued for at least 2 hours, but 4 hrs if the drug effect was still present at 2 hrs. In cases where animals were used repeatedly, a minimum of three washout days followed each test session. Responses were sampled once every 20 sec throughout the experiment.

Test Compounds

Compound X was kept frozen at approximately −20° C. in a freezer as a powder. Immediately prior the powder was dissolved in double distilled water (ddw) to make a 12 mg/ml stock and then diluted by 50% for injection at 6 mg/kg at a final volume of 1 ml/kg.

Physostigmine (eserine hemisulfate) was purchased from Sigma Aldrich and dissolved in ddw to make a 1 mg/ml stock solution. For injection the stock was diluted 10× and administered at 0.1 mg/kg at a final volume of 1 ml/kg. Galantamine (galantamine hydro bromide) was purchased from Sigma Aldrich and dissolved in ddw to make a 2 mg/ml stock solution. For injection the stock was diluted by 50% and administered at 1 mg/kg at a final volume of 1 ml/kg.

For combination treatment of Compound X and physostigmine the 12 mg/ml stock solution of Compound X and the 1 mg/ml stock of physostigmine were diluted by 50% and 10%, respectively, and injected at a final volume of 1 ml/kg. For combination treatment of Compound X and galantamine, the 12 mg/ml stock solution of Compound X and the 2 mg/ml stock of galantamine were each diluted by 50% and injected at a final volume of 1 ml/kg.

All compounds were injected intraperitoneally (ip).

Calculations

All electrophysiological data were collected and digitized by NacGather 2.0.7.2 Neurodata Acquisition Systems, and then analyzed using NacShow and graphed using GraphPad Prism. All results were expressed relative to fEPSP amplitude values across the 15 min baseline period preceding vehicle injection and are presented as means±SEM. For drug effects on excitatory synaptic transmission (fEPSP amplitude), statistical comparisons were done for each compound separately, using paired two-tailed t-tests between averaged data for the entire 15 min pre-drug vehicle period vs. averaged data over a 15 min post-drug period identified as showing the largest increase. Statistical comparisons between facilitatory effects of combination treatments (Compound X with physostigmine or Compound X plus galantamine) vs Compound X alone or cholinesterase inhibitors alone, respectively, were done using unpaired one-tailed t-tests between post-drug peak values averaged over 15 min. The significance value was set at $p<0.05$ (indicated by *), $p<0.01$ (indicated by ) and $p<0.001$ (indicated by *).

Results

Figure 1:
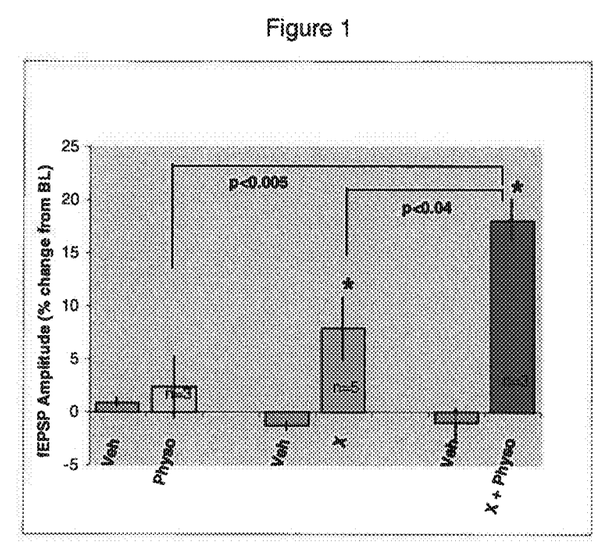
FIG. 1 shows the effect of Compound X on hippocampal fEPSP amplitude recorded in the freely moving rat compared to physostigmine alone and to physostigmine combined with Compound X. Statistical results for each treatment using within group comparisons are indicated by stars (for exact values see Table 1). Comparisons between treatments involved unpaired t-tests, the results of which are illustrated next to the respective connector lines (using unpaired t-tests across groups). BL=baseline before vehicle injection.

Table 1 shows the effect physostigmine, Compound X, and Compound X combined with physostigmine on hippocampal excitatory synaptic transmission in the freely moving rat. Drug effects were assessed by measuring changes in amplitude of the fEPSP in presence of drug relative to changes occurring following vehicle injection that immediately preceded drug administration. Both Compound X by itself, and co-applied with physostigmine, significantly enhanced hippocampal fEPSPs, in contrast to physostigmine which caused no significant alterations in basal transmission. Moreover, the facilitation produced by coapplication of Compound X with physostigmine was significantly larger than that observed with Compound X alone or physostigmine alone (see FIG. 1).

TABLE 1

| TREATMENT | DOSE (MG/KG) | VEHICLE $_F$EPSP AMPLITUDE [% OF PRE-VEHICLE BASELINE ± S.E.M.] | DRUG $_F$EPSP AMPLITUDE [% OF PRE-VEHICLE BASELINE ± S.E.M.] | P-VALUE (DRUG VS. VEHICLE) |
|---|---|---|---|---|
| Physostigmine | 0.1 | 0.86 + 0.49 | 2.33 + 2.91 | 0.62 |
| Compound X | 6.0 | −1.24 + 0.43 | 7.86 + 2.98 | 0.05* |
| Compound X plus Physostigmine | 6.0 plus 0.1 | −1.0 + 0.44 | 18.1 + 2.04 | 0.02* |

Table 1 shows Compound X at 6 mg/kg ip alone (n=5) and combined with physostigmine at 0.1 mg/kg ip (n=3) had significant facilitatory activity on basal excitatory synaptic transmission in the hippocampus of freely moving Sprague-Dawley rats. Physostigmine by itself (n=3) was inactive, demonstrating no significant enhancement of basal synaptic transmission. Individual t-test (two-tailed, paired) comparison values are shown.

Figure 2:
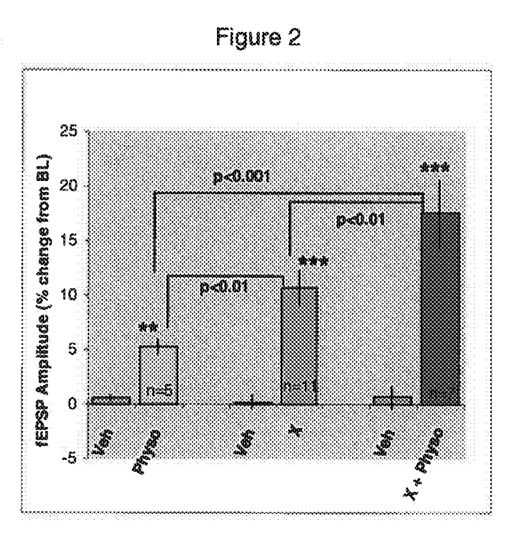
FIG. 2 shows the effect of Compound X on cortical fEPSP amplitude recorded in the freely moving rat compared to physostigmine alone and to physostigmine combined with Compound X. Statistical results for each of the three treatments using within group comparisons are indicated by stars (for exact values see Table 2). Comparisons between treatments involved unpaired t-tests, the results of which are illustrated next to the respective connector lines (using unpaired t-tests across groups).

Table 2 shows the effect physostigmine, Compound X, and Compound X combined with physostigmine on excitatory synaptic transmission in the olfactory cortex. Drug effects were assessed by measuring changes in amplitude of the fEPSP in presence of drug relative to changes occurring following vehicle injection that immediately preceded drug administration. Both Compound X by itself, and co-applied with physostigmine, significantly enhanced hippocampal fEPSPs. Physostigmine also caused a significant increase in basal transmission, but this effect was significantly smaller than that observed with Compound X alone or Compound X co-applied with physostigmine (see FIG. 2). In addition, the facilitation produced by co-application of Compound X plus physostigmine was significantly larger than that observed with Compound X alone (see FIG. 2).

TABLE 2

| TREATMENT | DOSE (MG/KG) | VEHICLE $_F$EPSP AMPLITUDE [% OF PRE-VEHICLE BASELINE ± S.E.M.] | DRUG $_F$EPSP AMPLITUDE [% OF PRE-VEHICLE BASELINE ± S.E.M.] | P-VALUE (DRUG VS. VEHICLE) |
|---|---|---|---|---|
| Physostigmine | 0.1 | 0.54 + 0.23 | 5.30 + 0.69 | 0.004** |
| Compound X | 6.0 | 0.17 + 0.60 | 10.67 + 1.67 | 0.00002*** |
| Compound X plus Physostigmine | 6.0 plus 0.1 | 0.64 + 1.00 | 17.51 + 3.06 | 0.0004** |

Table 2 shows that Compound X at 6 mg/kg ip alone (n=11) and combined with physostigmine at 0.1 mg/kg ip (n=7) had significant facilitatory activity on basal excitatory synaptic transmission in the olfactory cortex of freely moving Sprague-Dawley rats. Physostigmine by itself (n=5) also produced a significant enhancement of basal synaptic transmission. Individual t-test comparison values (two-tailed, paired) are shown. The facilitation produced by physostigmine alone was significantly smaller than that obtained both with Compound X alone or Compound X plus physostigmine combined.

Figure 3:
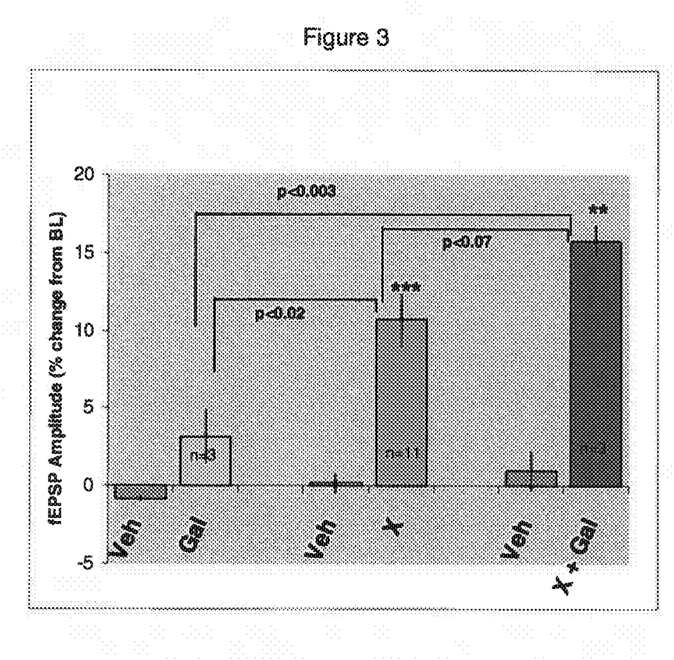
FIG. 3 shows the effect of Compound X on cortical fEPSP amplitude recorded in the freely moving rat compared to galantamine alone and to galantamine combined with Compound X. Statistical results for each of the three treatments using within group comparisons are indicated by stars (for exact values see Table 3). Comparisons between treatments involved unpaired t-tests, the results of which are illustrated next to the respective connector lines (using unpaired t-tests across groups).

Table 3 shows the effect galantamine, Compound X, and Compound X combined with galantamine on excitatory synaptic transmission in the olfactory cortex. Drug effects were assessed by measuring changes in amplitude of the fEPSP in presence of drug relative to changes occurring following vehicle injection preceding drug administration. Both Compound X by itself, and Compound X co-applied with galantamine, significantly enhanced hippocampal fEPSPs, in contrast to galantamine which caused no significant alterations in basal transmission. The facilitation produced by the co-application of Compound X plus galantamine was substantially larger than that observed with Compound X alone, but did not reach significance levels (p=0.07) (see FIG. 3).

TABLE 3

| TREATMENT | DOSE (MG/KG) | VEHICLE $_F$EPSP AMPLITUDE [% OF PRE-VEHICLE BASELINE ± S.E.M.] | DRUG $_F$EPSP AMPLITUDE [% OF PRE-VEHICLE BASELINE ± S.E.M.] | P-VALUE (DRUG VS. VEHICLE) |
|---|---|---|---|---|
| Galantamine | 1.0 | −.90 + 0.15 | 3.13 + 1.73 | 0.16 |
| Compound X | 6.0 | 0.17 + 0.60 | 10.67 + 1.67 | 0.00002*** |
| Compound X plus Galantamine | 6.0 plus 1.0 | 0.96 + 1.23 | 15.76 + 0.98 | 0.004** |

Table 3 shows that Compound X at 6 mg/kg ip alone (n=11) and combined with galantamine at 1 mg/kg ip (n=3) had significant facilitatory activity on basal excitatory synaptic transmission in the olfactory cortex of freely moving Sprague-Dawley rats. Galantamine by itself at 1 mg/kg (n=3) was inactive, demonstrating no significant enhancement of basal synaptic transmission. Individual t-test comparison values are shown (two-tailed, paired).

These experiments show that Compound X, at a dose which enhances memory in rodents, produced a significant increase in basal hippocampal and cortical excitatory synaptic transmission, a measure positively associated with behavioral performance and learning. This response of Compound X in the freely moving rat was significantly enhanced by co-administration of subthreshold doses of either physostigmine or galantamine in both hippocampus and olfactory cortex, and to a similar degree. Physostigmine and galantamine by themselves at the same dose did not affect basal transmission. These results demonstrate that Compound X can magnify or synergize with physostigmine and galantamine.

Example 2

The compositions of the invention are exemplified further in the table below.

| COMPOUND A | COMPOUND B | AMINISTERED |
|---|---|---|
| Donepezil | [structure: 3-pyridyl, OH, NH₂, pyrrolidine amide] | 0.5 mg Compound A + 50 mg Compound B formulated in a single tablet administered twice daily |
| Donepezil | [structure: 4-pyridyl, OH, NH₂, piperidine amide] | 1.0 mg Compound A administered once daily in the morning and evening + 50 mg Compound B administered once daily at mid day |
| Donepezil | [structure: 4-pyridyl, OH, NH₂, piperidine amide] | 2.5 mg Compound A + 30 mg Compound B formulated together in a solution administered once daily |
| Donepezil | [structure: 4-pyridyl, OH, NH₂, piperidine amide] | 10 mg Compound A + 30 mg Compound B formulated together in a solution administered once daily |
| Galantamine | [structure: 3-thienyl, OH, NH₂, piperidine amide] | 4 mg Compound A + 25 mg Compound B formulated in a single tablet and administered twice daily |
| Galantamine | [structure: 3-furyl, OH, NH₂, pyrrolidine amide] | One tablet containing 2 mg Compound A + one tablet containing 50 mg Compound B administered at the same time twice daily |
| Galantamine | [structure: 4-quinolinyl, OH, NH₂, pyrrolidine amide] | 4 mg Compound A administered once daily in the morning + 100 mg Compound B administered once daily in the evening |
| Galantamine | [structure: 4-quinolinyl, OH, NH₂, pyrrolidine amide] | 15 mg Compound A administered two daily + 30 mg Compound B administered once daily in the evening |
| Rivastigmine | [structure: 4-methylphenyl, OH, NH₂, pyrrolidine amide] | 0.5 mg Compound A + 50 mg Compound B formulated in a single tablet administered twice daily |

| COMPOUND A | COMPOUND B | AMINISTERED |
|---|---|---|
| Rivastigmine |  (biphenyl compound, not in crops above - shown at top of table) | 0.25 mg Compound A + 15 mg Compound B formulated together in a solution administered three times daily |
| Rivastigmine | (3-pyridyl compound with pyrrolidine) | One tablet containing 3 mg Compound A + one tablet containing 100 mg Compound B administered at the same time once daily |
| Rivastigmine | (3-thienyl compound with pyrrolidine) | 3 mg Compound A + 100 mg Compound B formulated in a single tablet administered once daily |
| Rivastigmine | (4-pyridyl compound with pyrrolidine) | 10 mg Compound A + one tablet containing 30 mg Compound B formulated in a single tablet administered once daily |

The method of the invention may be summarized as follows.

1. A pharmaceutical composition comprising a pharmaceutically effective cholinesterase inhibitor and a compound of Formula I:

wherein X is $CH_2$ or $CH_2$—$CH_2$,

A is aryl, or is heteroaryl having 0, 1, 2, or 3 heteroatoms selected from the group consisting of N, S, and O, wherein A has 0, 1, 2, or 3 substituents each comprising 0 to 8 carbon atoms, 0 to 3 oxygen atoms, 0 to 3 halogen atoms, 0 to 2 nitrogen atoms, 0 to 2 sulfur atoms, and 0 to 24 hydrogen atoms.

2. The pharmaceutical composition of 1, wherein A is selected from the group consisting of pyridinyl, thienyl, furyl, quinolinyl, methylphenyl, and biphenyl.

3. The pharmaceutical composition of 2, wherein A is unsubstituted.

4. The pharmaceutical composition of 1, wherein the compound of Formula I is selected from the group consisting of

and enantiomers and pharmaceutically acceptable salts thereof.

5. The pharmaceutical composition of any of 1-4, wherein the cholinesterase inhibitor is selected from the group consisting of donepezil, galantamine, and rivastigmine.

6. A method of treating a cognitive disorder, the method comprising administering to a human in need of such a treatment a pharmaceutical composition comprising a pharmaceutically effective cholinesterase inhibitor and a compound of Formula I:

wherein X is $CH_2$ or $CH_2$—$CH_2$,
A is aryl, or is heteroaryl having 0, 1, 2, or 3 heteroatoms selected from the group consisting of N, S, and O,
wherein A has 0, 1, 2, or 3 substituents each comprising 0 to 8 carbon atoms, 0 to 3 oxygen atoms, 0 to 3 halogen atoms, 0 to 2 nitrogen atoms, 0 to 2 sulfur atoms, and 0 to 24 hydrogen atoms.

7. The method of 6, wherein A is selected from the group consisting of pyridinyl, thienyl, furyl, quinolinyl, methylphenyl, and biphenyl.

8. The method of 7, wherein A is unsubstituted.

9. The method of 6, wherein the compound of Formula I is selected from the group consisting of and enantiomers and pharmaceutically acceptable salts thereof.

10. The method of any of 6-9, wherein the cholinesterase inhibitor is selected from the group consisting of donepezil, galantamine, and rivastigmine.

11. The method of any of 6-10, wherein the cognitive disorder is selected from the group consisting of an agnosia, an amnesias, an aphasias, an apraxias, a delirium, a dementia, and a learning disorder.

12. A method of treating a cognitive disorder, the method comprising administering to a patient in need of such a treatment a first composition comprising a pharmaceutically effective cholinesterase inhibitor and a second composition comprising compound of Formula I:

wherein X is CH$_2$ or CH$_2$—CH$_2$,

A is aryl, or is heteroaryl having 0, 1, 2, or 3 heteroatoms selected from the group consisting of N, S, and O, wherein A has 0, 1, 2, or 3 substituents each comprising 0 to 8 carbon atoms, 0 to 3 oxygen atoms, 0 to 3 halogen atoms, 0 to 2 nitrogen atoms, 0 to 2 sulfur atoms, and 0 to 24 hydrogen atoms.

13. The method of 12, wherein A is selected from the group consisting of pyridinyl, thienyl, furyl, quinolinyl, methylphenyl, and biphenyl.

14. The method of 13, wherein A is unsubstituted.

15. The method of 12, wherein the compound of Formula I is selected from the group consisting of and enantiomers and pharmaceutically acceptable salts thereof.

16. The method of any of 12-15, wherein the cholinesterase inhibitor is selected from the group consisting of donepezil, galantamine, and rivastigmine.

17. The method of any of 12-16, wherein the cognitive disorder is selected from the group consisting of an agnosia, an amnesia, an aphasia, an apraxia, a delirium, a dementia, and a learning disorder.

18. A method of treating dementia, the method comprising administering to a patient in need of such treatment a pharmaceutical composition comprising a) a pharmaceutically effective cholinesterase inhibitor selected from the group consisting of donepezil, galantamine, and rivastigmine; and b) a compound selected from the group consisting of

-continued and pharmaceutically acceptable salts thereof.

What is claimed is:

1. A method of treating dementia, the method comprising administering to a patient in need of such treatment a pharmaceutical composition comprising:
   a) a cholinesterase inhibitor selected from the group consisting of galantamine and physostigmine; and
   b) a compound of Formula I:

or a pharmaceutically acceptable salt thereof; wherein said cholinesterase inhibitor is administered at a dose that is ineffective or minimally effective to treat said dementia when administered alone.

2. The method of claim 1, wherein the cholinesterase inhibitor magnifies the pro-cognitive effect of the compound of Formula I or the pharmaceutically acceptable salt thereof.

3. The method of claim 1, wherein the cholinesterase inhibitor is galantamine.

4. The method of claim 1, wherein the cholinesterase inhibitor is physostigmine.

5. The method of claim 2, wherein the cholinesterase inhibitor is galantamine.

6. The method of claim 2, wherein the cholinesterase inhibitor is physostigmine.

* * * * *